United States Patent [19]

Burns et al.

[11] Patent Number: 4,526,754
[45] Date of Patent: Jul. 2, 1985

[54] SAMPLE TRANSPORT SYSTEM

[75] Inventors: Donald A. Burns, Putnam Valley; Marvin Margoshes, Tarrytown; Michael M. Cassaday, Peekskill, all of N.Y.

[73] Assignee: Technicon Instruments Corporation, Tarrytown, N.Y.

[21] Appl. No.: 403,886

[22] Filed: Jul. 30, 1982

[51] Int. Cl.³ .............................................. G01N 35/08
[52] U.S. Cl. .......................................... 422/82; 436/53
[58] Field of Search ...................... 422/81, 82; 436/52, 436/53

[56] References Cited

U.S. PATENT DOCUMENTS

| 3,134,263 | 5/1964 | De Jong | 73/864.25 |
| 3,479,141 | 11/1969 | Smythe et al. | 436/53 |
| 3,600,953 | 8/1971 | Isreeli et al. | 422/82 X |
| 3,790,348 | 2/1974 | Bossart et al. | 436/154 X |
| 3,921,439 | 11/1975 | Burns | 422/82 X |
| 4,009,999 | 3/1977 | Negersmith | 436/53 |
| 4,253,846 | 3/1981 | Smythe et al. | 436/53 |
| 4,259,291 | 3/1981 | Smythe | 422/82 |
| 4,399,102 | 8/1983 | Karlberg et al. | 422/82 |

Primary Examiner—Barry S. Richman
Assistant Examiner—Robert J. Hill, Jr.
Attorney, Agent, or Firm—S. P. Tedesco

[57] ABSTRACT

A transport system is provided in which a plurality of samples are introduced into a carrier stream flowing through a conduit, whose inner surface is coated with an immiscible liquid film. The carrier stream can be a sequence of alternating gas and liquid segments which are in direct contact with each other and, thus, not encompassed by the immiscible liquid. Samples are introduced at various points along the conduit and, thus, the system allows for the collection and transport of samples from a plurality of remote locations to at least one central receiving station where they can, for example, be analyzed. Carryover between successive samples to be transported is effectively eliminated.

7 Claims, 6 Drawing Figures

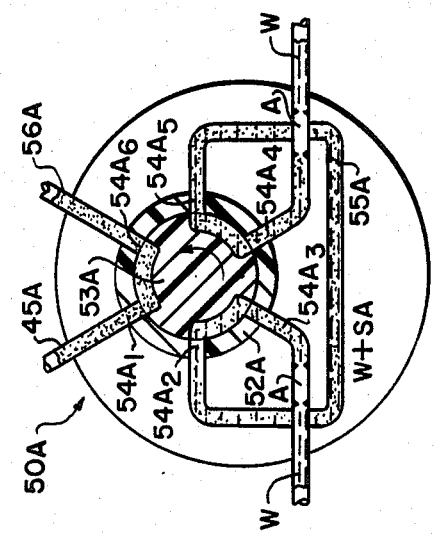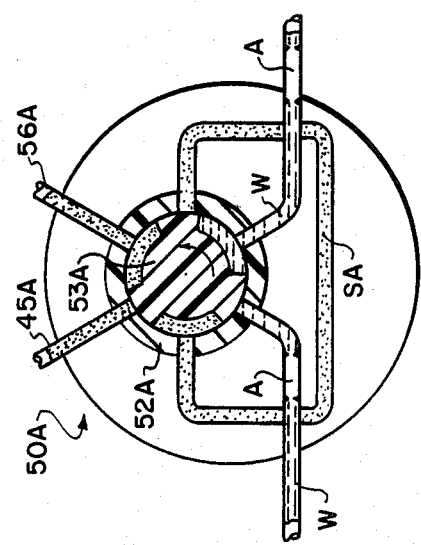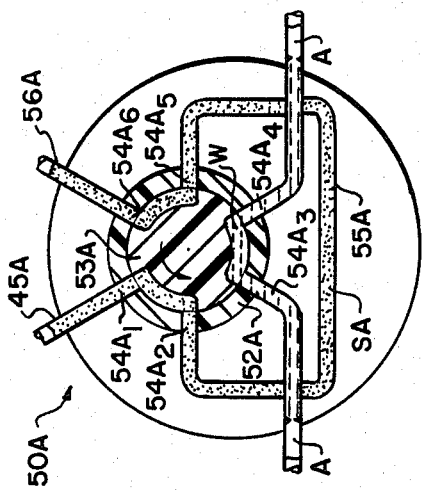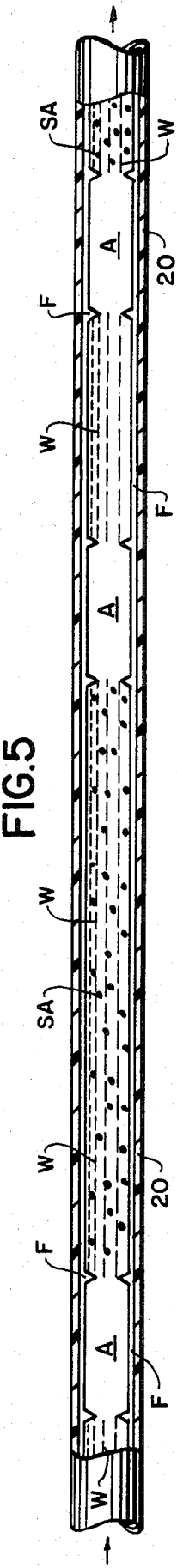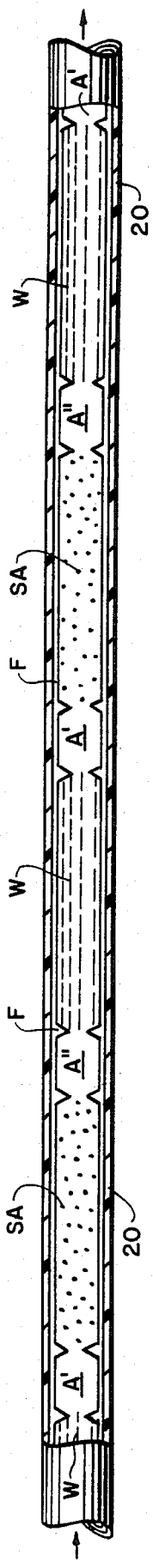

SAMPLE TRANSPORT SYSTEM

BACKGROUND OF THE INVENTION

1. Field of the Invention

The present invention relates to a system for introducing, segregating and transporting samples to be analyzed, such as industrial or biological samples, through a conduit.

2. Brief Description of the Prior Art

Automated apparatus for the analysis of liquid samples as a flowing stream was disclosed in U.S. Pat. Nos. 2,797,149 and 2,879,141, both assigned to the instant assignee. In this basic apparatus, the liquid samples are sequentially aspirated from containers located on a turntable arrangement and into a conduit, each sample being separated from the next successive sample by a segment of air. Customarily, the conduit is made of glass, rubber or polyvinylchloride. As the aqueous liquid samples wet the inner surface of the conduit, a residue or thin film of sample liquid adheres to the surface during passage along the conduit. This adhered liquid film is, in part, taken up by the next successive liquid segment, which is thereby contaminated. Various expedients have been successfully utilized to reduce this intersegment contamination.

U.S. Pat. No. 3,479,141, assigned to the instant assignee, discloses an automated analytical apparatus wherein a series of aqueous liquid samples are processed as a flowing stream with substantially no contamination between samples by the mixing of a portion of a prior sample with a succeeding sample (carryover). In such apparatus, a liquid, which is immiscible with the liquid samples and which preferentially wets the interior conduit wall, is referred to as a carrier fluid and is used to pass the successive samples along the conduit. The individual samples are encapsulated in the immiscible liquid and do not contact the conduit wall, whereby no sample residue adheres to the wall and contamination of a next liquid sample is avoided. The individual sample segments are surrounded by and flow in a stream of the immiscible liquid, which can be silicone. An air segment can be provided between sample segments and within the immiscible fluid to insure that successive sample segments do not coalesce.

U.S. Pat. No. 4,253,846 describes a system wherein discrete liquid sample segments are conveyed along a conduit in an immiscible liquid stream, as described in U.S. Pat. No. 3,479,141, above. As in U.S. Pat. No. 3,479,141, cited above, the immiscible fluid fully encapsulates each sample segment which is passed along the system. In such a system, reagents are injected, on a selected basis, into the successive liquid samples as they are passed along a portion of the conduit, so as to react with the same. U.S. Pat. No. 4,259,291, also assigned to the instant assignee, illustrates a mode of introducing sample to establish a stream of alternating gas and liquid segments to which diluent is later added.

Each of the above-described systems does involve the transport of liquid samples along a conduit. However, the overall or total conduit length of such systems is usually not greater than about 10 feet. Also, such systems are characterized in that the liquid samples to be analyzed have been previously collected, usually by technicians, from various sources or patients and brought to a single location for introduction into the continuous-flow system, e.g. an indexing turntable from which the samples are successively aspirated into the system. The gathering of such samples is not only costly and time-consuming, but, also, is a source of human error in respect of sample identification.

Accordingly, whether in a clinical or industrial environment, there is a need for a reliable and inexpensive technique for gathering and transporting samples from remote locations to a centrally located analytical station, without human intervention. Also, for monitoring purposes, as in the case of various industrial processes throughout a manufacturing establishment, it is advantageous to be able to periodically monitor one or more remote locations by having samples of an industrial material analyzed at a centrally located analytical station. Heretofore, it has been necessary to provide an analytical station at each such remote location. The present invention is directed to overcoming such requirements and provides a single, centralized analytical station which can service a plurality of remote stations.

SUMMARY OF THE INVENTION

According to the present invention, contamination between successive segments of a sample transported along a continuous-flow system is avoided by coating the conduit walls with a thin film of an immiscible fluid. The sample, which may be liquid or gaseous, is carried in a carrier stream, passed along the conduit, over the film or coating. The carrier stream can be an alternating sequence of gas and liquid segments which are in direct contact with each other and, thus, not encompassed by the immiscible fluid. The immiscible fluid is chemically inert to the samples to be transported. The individual samples can be introduced along the conduit at selected times and at selected points spaced apart, e.g. remote, from a receiving station which can include or be incorporated in an analyzer. A remote location within the contemplation of the invention can be at least 120 to 150 yards. The flow rate achieved can be up to 1 foot/second or more.

Accordingly, the present invention provides a system for transporting in a carrier stream a plurality of samples to be analyzed in at least one analyzer, which system comprises (a) a conduit having an inner surface coated with a continuous film of a liquid, said liquid being immiscible with said carrier stream and said samples and preferentially wetting said inner surface; (b) means for passing a carrier stream, which is uninterrupted by said immiscible liquid, through said conduit; (c) means for introducing each of said samples to be transported into said carrier stream at separate locations along said conduit and spaced apart from said at least one analyzer; and (d) at least one receiving station in fluid communication with said conduit for receiving said samples to be analyzed. The carrier stream may be formed of alternating gas and liquid segments. Preferably, the gas segments alternate in a regular sequence with liquid segments of substantially uniform volume.

The invention further provides a method for transporting in a carrier stream a plurality of samples to be analyzed in at least one analyzer, which method comprises (a) passing a carrier stream through a conduit having an inner surface coated with a continuous film of a liquid which is immiscible with said carrier stream and said samples and which preferentially wets said inner surface, said carrier stream being uninterrupted by said immiscible liquid; and (b) introducing each of said samples to be transported into said carrier stream at separate locations along said conduit and spaced apart from said at least one analyzer.

BRIEF DESCRIPTION OF THE DRAWINGS

FIG. 2 is an enlarged view of an injector configuration to receive a sample from a fermentor into the injector.

FIG. 3 is an enlarged view of an injector configuration which has been rotated from that configuration in which a sample is received from a fermentor into the injector and is being rotated to that configuration in which a sample is introduced into a transport conduit from the injector.

FIG. 4 is an enlarged view of an injector configuration to introduce a sample into a transport conduit from the injector.

FIG. 5 is a cut-away view of a transport conduit showing an immiscible fluid film on the inner surface thereof and an uninterrupted air/liquid alternating segment carrier stream with the sample being transported in a liquid segment.

FIG. 6 is a cut-away view of a transport conduit showing an immiscible fluid film on the inner surface and an uninterrupted air/liquid alternating segment carrier stream with the sample being transported positioned between two subdivided portions of an air segment.

DESCRIPTION OF THE PREFERRED EMBODIMENTS

Figure 1:
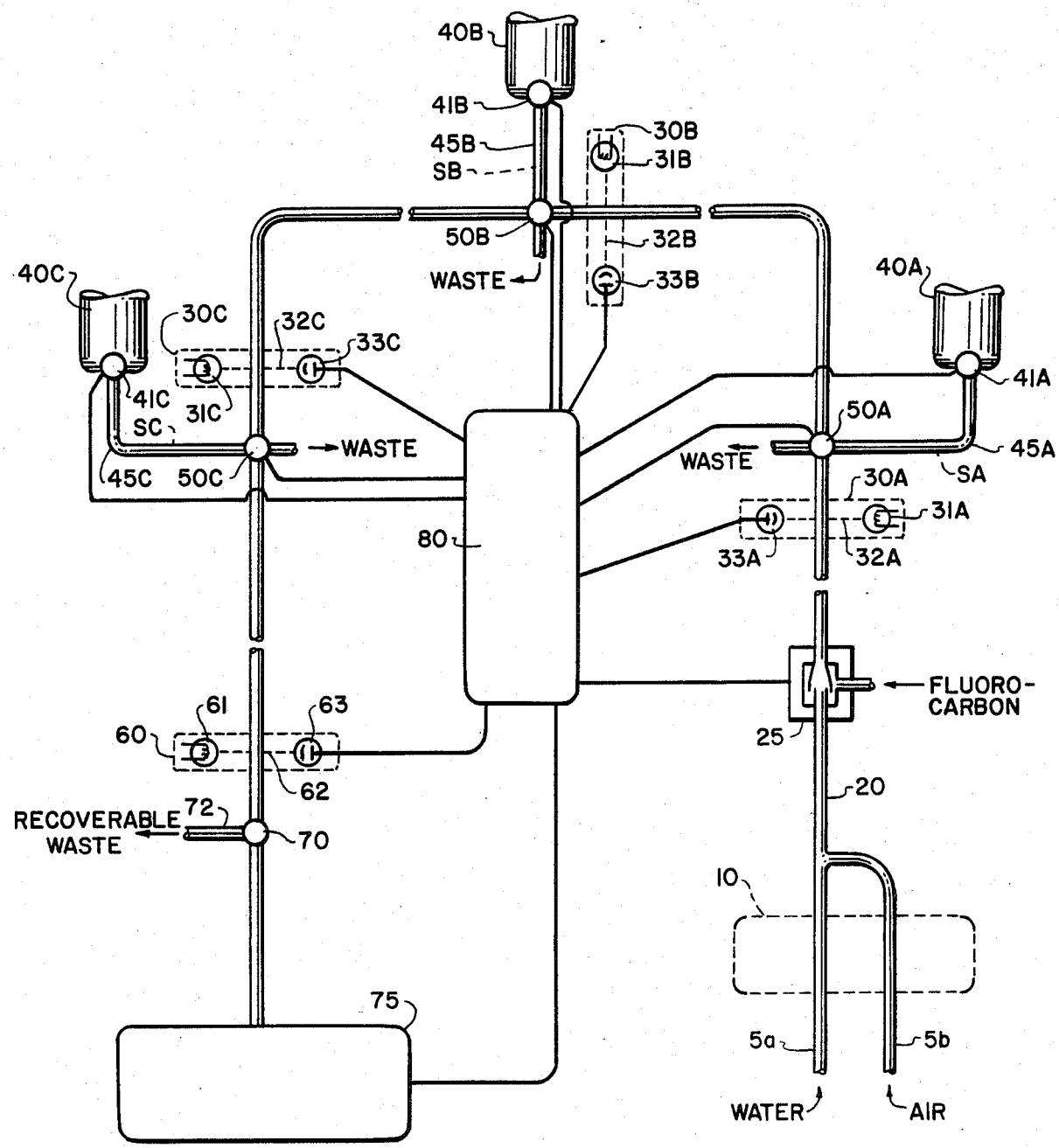
FIG. 1 is a schematic diagram of a preferred embodiment of the transport system of the present invention.

Although specific terms are used in the following description for clarity, they refer only to the particular embodiment(s) selected for illustration, and are not intended to limit the scope of the invention.

The transport system of the present invention is particularly suitable for carrying liquid samples along a conduit from a plurality of remote locations to a continuous-flow analyzer, of the type disclosed in U.S. Pat. No. 3,479,141, discussed above. The liquid samples can be industrial liquids, for example, specimens from fermentation containers such as are used in the manufacture of food, drink, pharmaceuticals and industrial chemicals, or can be blood, serum, urine, cerebrospinal fluid, tissue culture supernatant, and the like. The liquid samples are introduced at selected times and at different points along the length of the conduit, which is coated with a film of the immiscible liquid and along which an aqueous carrier stream is passed. If desired, such samples can be introduced directly through the conduit wall and immiscible coating, which reforms substantially immediately.

As shown in FIG. 1, the transport system of the invention has adapted continuous-flow technology to sample transport. A continuous stream of carrier liquid, e.g. water, is introduced into the transport system at a rate of, for example, 30 milliliters per minute or more through pump tube 5a of peristaltic pump 10 (shown in phantom). The outlet of pump tube 5a is connected to conduit 20. Air is continuously passed through pump tube 5b. Peristaltic pump 10 may include an "air-bar" arrangement, as disclosed in U.S. Pat. No. 3,306,229. The "air-bar" is a blunt blade which pinches pump tube 5b to control the introduction of air bubbles into conduit 20 at regular intervals synchronized with the operation of pump 10, to form an alternating sequence of air and water segments. This achieves uniformity of water segment volume. A typical volume of air bubbles under normal atmospheric pressure is about 17 microliters, a typical water segment is about 500 microliters and the inner diameter of conduit 20 is typically from about 0.5 to about 1.5 millimeters. Conduit 20 can be formed, for example, of polytetrafluoroethylene.

The carrier stream so formed flows through dispenser 25 which is controlled by controller 80, to feed immiscible fluid into conduit 20 so as to establish and maintain a continuous film of immiscible fluid on the inner surface of conduit 20. Once the immiscible film is established, dispenser 25 feeds immiscible fluid into conduit 20, either intermittently or continuously, at a rate sufficient to maintain such film. The interface between the gas and liquid segments of the carrier stream, in what is referred to as a "paintbrush" effect, carries a "fillet" of immiscible liquid with it which spreads the immiscible liquid so as to coat the inner walls of conduit 20. Silicone or liquid fluorocarbons are suitable immiscible liquid film materials where the conduit is of a fluorinated hydrocarbon polymer, such as a tetrafluoroethylene polymer. A hydrocarbon oil, such as squalene, is a suitable material where the conduit is polypropylene. The coating of immiscible liquid preferentially wets the inner walls to the exclusion of both the aqueous samples to be transported and the aqueous carrier stream.

A plurality of fermentors 40A-40C are positioned along conduit 20 and samples are taken from each in like manner. Therefore, this aspect of the system will be described with respect to fermentor 40A, injector 50A, and related apparatus as representative. Fermentor 40A opens into sample supply tube 45A either continuously or through a valve 41A which is opened by command from controller 80 when a sample SA is desired. Sample SA passes through sample supply tube 45A and into injector 50A.

Photodetector 30A is located immediately upstream of injector 50A and comprises a light source 31 and a photocell 33. Photodetector 30A senses the passage of the air/liquid interface through light path 32 and sends a signal to controller 80 which, in turn, activates injector 50A. A precisely defined aliquot of sample SA is thereby introduced into the carrier stream in synchronization with the passage of air and water segments. The details of injector 50A and its operation in injecting sample SA into liquid and air segments is described in more detail below. Additionally, controller 80 coordinates the timing of operation between different injectors to insure that a later, or downstream, injector is not activated during passage therethrough of a sample which has been injected by any upstream injector. It should be appreciated that these fermentors can be spaced apart by great distances. Indeed, they can even be in separate buildings, if desired. It is, therefore, sometimes desirable to transport samples over longer distances than are possible without undue pumping pressures. In such cases, a valve (not shown) of the same type as is used for injectors 50A–50C can be used to select a portion of the flowing stream containing the sample segment and insert that portion into the start of a second carrier stream. In this way, the distance that a sample may be transported can be extended indefinitely.

A photodetector 60 is located downstream of the last injector 50C and comprises a light source 61 and a photocell 63. Photodetector 60 senses the passage of the leading edge of each segment of sample SA passing through light path 62 and sends a signal to controller 80. As the sequence and respective times of introduction, which may be both random, are known, the alerting of controller 80 by photodetector 60 is sufficient for controller 80 to identify the detected sample segment in respect of the particular fermentor 40A–40C from which it was supplied and, also, to control valve 70 and analyzer 75 to analyze the same.

Recovery valve 70 normally directs the carrier stream to recoverable waste along waste tube 72. In this way, expensive immiscible liquid (e.g. fluorocarbon) can be salvaged for reuse. In response to the detection of sample SA by photodetector 60, carrier stream recovery valve 70 diverts the flow along conduit 20 and causes a portion of the carrier stream containing the sample SA to flow to analyzer 75 for analysis in known fashion. Controller 80 can also be used to correlate the results obtained by analyzer 75 with respect to the particular fermentor from which it was obtained. Hence, a complete record of the fermentors 40A–40C can be obtained automatically and without human intervention. Alternatively, valve 70 can divert the flow to a collection point (not shown) that is not physically connected with an analyzer. Also, valve 70 may divert the stream alternately to any of a plurality of analyzers or collection points.

As best seen in FIG. 2, the carrier stream flowing in conduit 20 passes, without interruption, through any one of injectors 50A–50C which are identical six-port valves. Injector 50A is illustrated to exemplify these injectors. As shown, fermentor tube 45A receives sample SA from fermentor 40A (not shown) and is connected to sample inlet port 54A. Sample SA flows from port 54A, through ports $54A_2$, $54A_5$ and $54A_6$ and out to waste through waste tube 56A. A sample loop 55A between ports $54A_2$ and $54A_5$ has a storage capacity, typically, from about 2 milliliters (ml) to about 50 ml. As is conventional, the injector 50A comprises a valve sleeve 52A and rotating grooved stem 53A for the control of fluid flow. The inner walls of the grooves and ports can be of the same polytetrafluoroethylene material as the inner walls of transport conduit 20. Such valves are commercially available from, among others, Laboratory Data Control Division of Milton Roy Company, Riviera Beach, Florida 33404.

FIG. 3 shows injector 50A in a configuration which has been rotated from that configuration (position) in which sample SA is received from fermentor 40A into injector 50A and is being rotated to that configuration (position) in which a sample SA is introduced into a transport conduit 20 from the injector 50A. Grooved stem 53A is shown rotated through approximately a 30° angle. As such, movement of both sample and carrier fluid is arrested during this momentary transition to the configuration in which sample loop 55A is connected with conduit 20, as discussed more fully below.

With continuing reference to injector 50A in FIG. 4, grooved stem 53A is shown rotated through a 60° angle to connect sample loop 55A with conduit 20. Thus, a predetermined volume of sample SA in sample loop 55A is introduced into the carrier stream along conduit 20. In the valve position shown, sample SA being fed from fermentor tube 45A is passed directly from valve port 54A to port $54A_6$ and to waste through waste tube 56A. It can alternately be returned to the fermentor, if desired.

FIG. 5 depicts the passage of a carrier stream comprising air segments A and water segments W through a section of conduit 20, in the direction indicated by the arrow. The inner surface of conduit 20 is coated with a film F of fluorocarbon and the conduit is formed of polytetrafluoroethylene tubing. Sample SA is transported in water W, and is thus diluted to a known extent based on the relative liquid volumes of sample SA and water W. Following the segment of water W and sample SA is an immiscible segment of air A which, even in the absence of an interrupting or intervening fluorocarbon F barrier, maintains the liquid segment discrete from succeeding liquid segments. As is illustrated, liquid segments containing sample are usually alternated with liquid segments without sample.

FIG. 6 also depicts the passage of air segments A and water segments W of a carrier stream through conduit 20, in the direction indicated by the arrow. Again, the inner surface of conduit 20 is coated with a film F of fluorocarbon and conduit 20 is formed of polytetrafluoroethylene tubing. Sample segment SA is introduced so as to intersect air segment A thus forming two subdivided air segments A' and A" surrounding the point of sample introduction. Thus, it is necessary that air segment A which is to be intersected is long enough to extend across injector 40A and into at least a small portion of conduit 20, both upstream and downstream, of injector 40A. The subdivided segments A' and A" of air segment maintain the sample SA discrete from other segments in the substance transport system.

Although the invention has been described with particularity, numerous changes in the details, combinations and arrangements of elements may be resorted to without departing from the scope of the invention.

What is claimed is:

1. A system for transporting in a carrier stream a plurality of liquid samples to be analyzed in at least one analyzer located at a receiving station, which comprises:
   (a) a conduit having an inner surface;
   (b) means for establishing and maintaining on said inner surface of said conduit a continuous coating of a first liquid, said first liquid being immiscible with a carrier stream and a plurality of liquid samples and preferentially wetting said inner surface;
   (c) means for establishing and passing said carrier stream through said conduit, said carrier stream comprising an alternating sequence of gas segments and segments of a second liquid immiscible with said coating of first liquid on said conduit, said carrier stream being uninterrupted by said first liquid;
   (d) a plurality of means for introducing said samples into selected ones of said gas segments of said carrier stream so as to intersect said selected gas segments said introducing means being located at spaced locations along said conduit; a detecting means which includes a detector associated with and positioned upstream of each of said sample introducing means for detecting the passage of said selected gas segments and generating respective signals in response thereto;
   (f) a receiving station including at least one analyzer and in fluid communication with said conduit for receiving said carrier stream and for analyzing said plurality of samples introduced therein in said at least one analyzer, said receiving station being spaced apart from said plurality of introducing means; and
   (g) control means for receiving said signals from said gas segment detectors and controlling said plurality of introducing means to introduce said samples so as to intersect said selected gas segments in response to said signals.

2. The system of claim 1 wherein said means for establishing and passing said carrier stream comprises means for passing a plurality of gas segments of substantially uniform volume in a regular alternating sequence with a plurality of segments of said second liquid of substantially uniform volume.

3. The system of claim 1 wherein said establishing and maintaining means includes means for introducing a fluorocarbon into said conduit at a rate sufficient to maintain said coating along said conduit during passage of said carrier stream.

4. The system of claim 1 wherein said detecting means further includes a sample detector associated with said receiving station and positioned along said conduit between each of said sample introducing means and said receiving station.

5. The system of claim 1 wherein each of said sample introducing means comprises a valve arrangement including a loop of predetermined volume at each of said spaced locations for introducing a sample into said carrier stream.

6. The system of claim 5 wherein said detecting means further includes means for detecting passage of said samples along said conduit, said sample detecting means being located between said means for establishing and passing said carrier stream and said receiving station.

7. A system for transporting in a carrier stream a plurality of aqueous liquid samples to be analyzed in an analyzer, which system comprises:

(a) a conduit having an inner surface;

(b) means for establishing and maintaining a continuous coating of fluorocarbon on said conduit surface;

(c) means for establishing and passing a carrier stream of alternating air and aqueous liquid segments immiscible with said fluorocarbon coating along said conduit, said carrier stream being uninterrupted by said fluorocarbon;

(d) a plurality of means for introducing a plurality of aqueous liquid samples into selected ones of said air segments of said carrier stream through said fluorocarbon coating at spaced locations along said conduit;

(e) an analyzer connected to said conduit for receiving said carrier stream and including a photometer for analyzing said plurality of aqueous liquid samples;

(f) a detecting means which includes at least one sample detector positioned along said conduit between said means for establishing and passing said carrier stream and said analyzer and a detector associated with and positioned upstream of each of said sample introducing means for detecting the passage of said selected gas segments and generating respective signals in response thereto;

(g) means for recovering any fluorocarbon forming said continuous coating which is passed through said conduit; and (h) control means for receiving said signals from said gas segment detectors and controlling said introducing means to introduce said aqueous liquid samples to intersect said selected air segments in response to said signals.

* * * * *